(12) United States Patent
Bogdan et al.

(10) Patent No.: US 7,525,008 B2
(45) Date of Patent: Apr. 28, 2009

(54) PROCESS FOR C8 ALKYLAROMATIC ISOMERIZATION

(75) Inventors: Paula L. Bogdan, Mount Prospect, IL (US); John E. Bauer, La Grange Park, IL (US); E. Alejandro Leon-Escamilla, Mount Prospect, IL (US); Gregory F. Maher, Aurora, IL (US); Robert B. Larson, Chicago, IL (US)

(73) Assignee: UOP LLC, Des Plaines, IL (US)

( * ) Notice: Subject to any disclaimer, the term of this patent is extended or adjusted under 35 U.S.C. 154(b) by 758 days.

(21) Appl. No.: 11/137,292

(22) Filed: May 25, 2005

(65) Prior Publication Data

US 2005/0277796 A1 Dec. 15, 2005

Related U.S. Application Data

(63) Continuation-in-part of application No. 10/749,156, filed on Dec. 30, 2003, now abandoned, and a continuation-in-part of application No. 10/749,179, filed on Dec. 30, 2003, now abandoned.

(51) Int. Cl.
  *C07C 5/29* (2006.01)
(52) U.S. Cl. .................. 585/481; 585/482; 585/480
(58) Field of Classification Search ................ 585/481, 585/480, 482
  See application file for complete search history.

(56) References Cited

U.S. PATENT DOCUMENTS

| | | | |
|---|---|---|---|
| 2,620,314 A | 12/1952 | Hoekstra | 252/448 |
| 3,201,491 A | 8/1965 | Stine et al. | 260/676 |
| 3,626,020 A | 12/1971 | Neuzil | 260/674 SA |
| 3,696,107 A | 10/1972 | Neuzil | 260/674 SA |
| 3,832,449 A | 8/1974 | Rosinski et al. | 423/328 |
| 3,856,871 A | 12/1974 | Haag et al. | 260/668 A |
| 3,856,872 A | 12/1974 | Morrison | 260/668 A |
| 4,016,219 A | 4/1977 | Kaeding | 260/672 T |
| 4,039,599 A | 8/1977 | Gewartowski | 260/668 A |
| 4,097,543 A | 6/1978 | Haag et al. | 260/672 T |
| 4,184,943 A | 1/1980 | Anderson | 208/310 R |
| 4,268,420 A | 5/1981 | Klotz | 252/432 |
| 4,331,822 A | 5/1982 | Onodera et al. | 585/482 |
| 4,341,914 A | 7/1982 | Berger | 585/474 |
| 4,381,419 A | 4/1983 | Wylie | 585/828 |
| 4,402,832 A | 9/1983 | Gerhold | 210/659 |
| 4,452,769 A | 6/1984 | Chu et al. | 423/329 |
| 4,537,758 A | 8/1985 | Chu et al. | 423/329 |
| 4,899,011 A | 2/1990 | Chu et al. | 585/481 |
| 4,899,012 A | 2/1990 | Sachtler et al. | 585/482 |
| 4,939,110 A | 7/1990 | Sachtler et al. | 502/66 |
| 4,943,424 A | 7/1990 | Miller | 423/328 |
| 4,962,258 A | 10/1990 | Amelse et al. | 585/480 |
| 4,962,259 A * | 10/1990 | Sachtler et al. | 585/480 |
| 5,081,084 A | 1/1992 | Sachtler et al. | 502/61 |
| 5,744,673 A | 4/1998 | Skeels et al. | 585/474 |
| 5,898,090 A | 4/1999 | Hammerman et al. | 885/477 |
| 6,057,486 A | 5/2000 | Merlen et al. | 585/481 |
| 6,143,941 A | 11/2000 | Sharma et al. | 585/481 |
| 6,465,705 B1 | 10/2002 | Merlen et al. | 585/481 |
| 6,652,832 B2 | 11/2003 | Malek | 423/706 |
| 6,797,849 B2 | 9/2004 | McMinn et al. | 585/319 |
| 6,872,866 B1 | 3/2005 | Nemeth et al. | 585/481 |

* cited by examiner

*Primary Examiner*—Thuan D Dang
(74) *Attorney, Agent, or Firm*—Maryann Maas

(57) ABSTRACT

A process for isomerizing ethylbenzene into xylenes such as para-xylene using a zeolitic catalyst system based on low $Si/Al_2$ MTW-type zeolite that preferably is substantially free of mordenite. The catalyst may be bimetallic where the two metals are platinum and tin.

15 Claims, No Drawings

PROCESS FOR C8 ALKYLAROMATIC ISOMERIZATION

CROSS-REFERENCE TO RELATED APPLICATIONS

This application is a Continuation-In Part of applications Ser. No. 10/749,156 and Ser. No. 10/749,179, both filed Dec. 30, 2003, both now abandoned, the contents of each are hereby incorporated by reference in its entirety.

FIELD OF THE INVENTION

The present invention relates to catalytic processes for the isomerization of xylenes and for the conversion of ethylbenzene in the presence of hydrogen.

BACKGROUND OF THE INVENTION

The xylenes, para-xylene, meta-xylene and ortho-xylene, are important intermediates that find wide and varied application in chemical syntheses. Para-xylene upon oxidation yields terephthalic acid that is used in the manufacture of synthetic textile fibers and resins. Meta-xylene is used in the manufacture of plasticizers, azo dyes, wood preservers, etc. Ortho-xylene is feedstock for phthalic anhydride production.

Xylene isomers from catalytic reforming or other sources generally do not match demand proportions as chemical intermediates, and further comprise ethylbenzene, which is difficult to separate or to convert. Para-xylene in particular is a major chemical intermediate with rapidly growing demand, but amounts to only 20-25% of a typical $C_8$ aromatics stream. Adjustment of isomer ratio to demand can be effected by combining xylene-isomer recovery, such as adsorption for para-xylene recovery, with isomerization to yield an additional quantity of the desired isomer. Isomerization converts a non-equilibrium mixture of the xylene isomers that is lean in the desired xylene isomer to a mixture approaching equilibrium concentrations.

In general, these xylene isomerization processes comprise contacting the xylene isomer sought to be isomerized with an isomerization catalyst under isomerization conditions. Various catalysts have been proposed for xylene isomerization. These catalysts include molecular sieves, especially molecular sieves contained in a refractory, inorganic oxide matrix. U.S. Pat. No. 4,899,012 discloses an alkylaromatic isomerization process based on a bimetallic pentasil-type zeolitic catalyst system that also produces benzene. U.S. Pat. No. 4,962,258 discloses a process for liquid phase xylene isomerization over gallium-containing, crystalline silicate molecular sieves as an improvement over aluminosilicate zeolites ZSM-5, ZSM-12 (MTW-type), and ZSM-21 as shown in U.S. Pat. No. 3,856,871. The '258 patent refers to borosilicate work, as exemplified in U.S. Pat. No. 4,268,420, and to zeolites of the large pore type such as faujasite or mordenite. U.S. Pat. No. 5,744,673 discloses an isomerization process using beta zeolite and exemplifies the use of gas-phase conditions with hydrogen. U.S. Pat. No. 5,898,090 discloses an isomerization process using crystalline silicoaluminophosphate molecular sieves. U.S. Pat. No. 6,465,705 discloses a mordenite catalyst for isomerization of aromatics that is modified by an IUPAC Group III element. U.S. Pat. No. 6,143,941, for instance, discloses oil dropped catalyst structures for xylene isomerization in which various molecular sieve structures are suggested including the MFI, MEL, EUO, FER, MFS, MTT, MTW, TON, MOR and FAU types of zeolites. The catalysts also contain a platinum group metal which may exist in the catalyst as the metal or as a compound such as an oxide, sulfide, halide or oxysulfide. U.S. Pat. Nos. 3,856,872; 4,899,011; 4,939,110 and 6,797,849 disclose, inter alia, MTW-type zeolites for xylene isomerization wherein the catalysts can contain at least one hydrogenation catalyst component.

Desirably the isomerization process as close to equilibrium as practical in order to maximize the para-xylene yield; however, associated with this is a greater cyclic $C_8$ loss due to side reactions. The approach to equilibrium that is used is an optimized compromise between high $C_8$ cyclic loss at high conversion (i.e., very close approach to equilibrium) and high utility costs due to the large recycle rate of unconverted $C_8$ aromatics. Catalysts thus are evaluated on the basis of a favorable balance of activity, selectivity and stability.

Due to the large scale of commercial facilities to produce para-xylene on an economically competitive basis, not only must a xylene isomerization process be active and stable, but it also must not unduly crack the aromatic feed so as to result in ring loss. Moreover, the isomerization processes produce by-products such as benzene, toluene, and aromatics having 9 or more carbon atoms. For instance, U.S. Pat. No. 6,872,866 discloses a liquid phase process using two catalysts for the isomerization of xylenes and ethylbenzene. The catalysts comprise beta zeolite and low $Si/Al_2$ MTW.

Often the xylene-containing feed to be isomerized also contains ethylbenzene. Ethylbenzene may be dealkylated such as would occur in the processes of U.S. Pat. No. 6,872,866, or the ethylbenzene can be converted. Advantageously, isomerization processes would convert ethylbenzene to xylenes. Whether the isomerization process will dealkylate or will convert ethylbenzene depends upon the isomerization conditions including catalyst.

Catalysts for isomerization of $C_8$ aromatics ordinarily are classified by the manner of processing ethylbenzene associated with the xylene isomers. Ethylbenzene is not easily isomerized to xylenes, but is normally converted in the isomerization unit because separation from the xylenes by superfractionation or adsorption is very expensive. A widely used approach is to dealkylate ethylbenzene to form principally benzene while isomerizing xylenes to a near-equilibrium mixture. An alternative approach is to react the ethylbenzene to form a xylene mixture via conversion to and reconversion from naphthenes in the presence of a solid acid catalyst with a hydrogenation-dehydrogenation function. The former approach commonly results in higher ethylbenzene conversion, thus lowering the quantity of recycle to the para-xylene recovery unit and concomitant processing costs, but the latter approach enhances xylene yield by forming xylenes from ethylbenzene. A catalyst composite and process which enhance conversion according to the latter approach, i.e., achieve ethylbenzene isomerization to xylenes with high conversion, would effect significant improvements in xylene-production economics.

Although numerous proposals have been made for catalyst and isomerization reactor schemes to achieve desired ethylbenzene conversion and xylene isomerization, the catalytic isomerization processes that are in commercial practice included both those that dealkylate and those that convert ethylbenzene. The commercially available catalysts for these isomerization processes are believed to be based upon EUO or ZSM-5 or MOR type zeolites in association with a hydrogenating catalytic component. Advantageously, improved catalysts that are capable of converting ethylbenzene would be capable of being readily retrofitted into such commercial processes.

SUMMARY OF THE INVENTION

The present invention provides a process for the isomerization of alkylaromatic hydrocarbons. More specifically, the process of the present invention is directed to $C_8$ aromatic hydrocarbons isomerization over certain catalysts containing MTW-type zeolite in order to convert ethylbenzene to xylenes and to obtain improved yields of desired xylene isomers.

The present invention is based on the discovery that a catalyst system comprising a low $Si/Al_2$ MTW-type zeolite, preferably substantially mordenite-free, with at least one hydrogenation catalytic component, and preferably a binder, demonstrates improved conversion and selectivity in $C_8$ aromatics isomerization, while minimizing undesired benzene formation. The catalyst may further comprise a Group IVA (IUPAC 14) component such as tin. Advantageously, the processes can benefit through low ring loss while still achieving desirable conversions of ethylbenzene and approaches to xylene equilibrium. Further those aromatic by-products formed during the isomerization tend to be those that can readily be converted to xylenes such as toluene and $C_9$ and $C_{10}$ aromatics.

The broad aspects of the processes of this invention comprise contacting a feed stream containing a non-equilibrium admixture of at least one xylene isomer and ethylbenzene wherein preferably between about 1 and 60, and more frequently between about 5 and 35, mass-% of the feed stream is ethylbenzene with a catalyst comprising MTW type zeolite having a silica/alumina mole ratio of between about 20:1 and 45:1 and a catalytically effective amount of at least one hydrogenation catalyst component, preferably a platinum group metal-containing component, under isomerization conditions. The isomerization conditions include the presence of hydrogen in a mole ratio to hydrocarbon of at least about 0.5:1, say, 0.5 to 6:1, preferably 1.5:1 to 5:1. Preferably, the feed stream contains naphthenes, and more preferably a sufficient concentration of naphthenes is provided in the feed stream to enhance the conversion of ethylbenzene, e.g., between about 2 and 20 mass-% naphthenes. Preferably, the isomerization is conducted under at least partially vapor phase conditions.

DETAILED DESCRIPTION OF THE INVENTION

The feedstocks to the aromatics isomerization processes of this invention comprise isomerizable alkylaromatic hydrocarbons of the general formula $C_6H_{(6-n)}R_n$, where n is an integer from 2 to 5 and R is $CH_3$, $C_2H_5$, $C_3H_7$, or $C_4H_9$, in any combination and including all the isomers thereof. Suitable alkylaromatic hydrocarbons include, for example but without so limiting the invention, ortho-xylene, meta-xylene, para-xylene, ethylbenzene, ethyltoluenes, tri-methylbenzenes, diethylbenzenes, triethylbenzenes, methylpropylbenzenes, ethylpropylbenzenes, di-isopropylbenzenes, and mixtures thereof.

A particularly preferred application of the catalyst system of the present invention is the isomerization of a $C_8$ aromatic mixture containing ethylbenzene and xylenes. Generally the mixture will have an ethylbenzene content of about 1 to about 60, preferably, about 1 to about 50 wt-%; an ortho-xylene content of 0 to about 35 wt-%; a meta-xylene content of about 20 to about 95 wt-% and a para-xylene content of 0 to about 30 wt-%. The $C_8$ aromatics are a non-equilibrium mixture, i.e., at least one $C_8$ aromatic isomer is present in a concentration that differs substantially from the equilibrium concentration at isomerization conditions. Usually the non-equilibrium mixture is prepared by removal of para-, ortho- and/or meta-xylene from a fresh $C_8$ aromatic mixture obtained from an aromatics-production process.

The alkylaromatic hydrocarbons may be utilized in the present invention as found in appropriate fractions from various refinery petroleum streams, such as individual components or as certain boiling-range fractions obtained by the selective fractionation and distillation of catalytically cracked or reformed hydrocarbons. The process of the present invention allows the isomerization of alkylaromatic-containing streams such as catalytic reformate with or without subsequent aromatics extraction to produce specified xylene isomers and particularly to produce para-xylene.

A $C_8$ aromatics feed to the present process may contain nonaromatic hydrocarbons, i.e., naphthenes and paraffins, in an amount up to about 30 wt-%, and preferably contains naphthenes in an amount sufficient to enhance the ethylbenzene conversion. Naphthenes are cyclic paraffins and may include, for purposes herein, cyclic compounds having non-aromatic unsaturation in the ring structure. A convenient source of naphthenes is the isomerization process itself which produces naphthenes. Typically the naphthenes that are recycled are monocyclic compounds, especially 5 and 6 carbon atom rings, having from 5 to 9 carbon atoms. The downstream unit operations will define the composition and amount of naphthenes being recycled. Generally, the naphthenes are present in an amount of about 2 to 20, preferably from about 4 to 15, wt-% of the feed. Equilibria may exist under isomerization conditions between naphthenes and aromatics. Thus, at isomerization conditions that convert a greater percentage of ethylbenzene, greater concentrations of naphthenes are preferred. As the naphthenes are a by-product of the isomerization, usually the isomerization unit is started up with the xylene and ethylbenzene feed and then the sought amount of naphthenes are permitted to build up for steady-state operation.

Preferably, the isomerizable hydrocarbons consist essentially of aromatics, to ensure pure products from downstream recovery processes. Moreover, a $C_8$ aromatics feed that is rich in undesired ethylbenzene can be supplied such that it can be converted to xylenes.

According to the process of the present invention, an alkylaromatic hydrocarbon feed mixture, in the presence of hydrogen, is contacted with a catalyst of the type described below in an alkylaromatic hydrocarbon isomerization zone. Contacting may be effected using the catalyst in a fixed-bed system, a moving-bed system, a fluidized-bed system, or in a batch-type operation. The fixed bed operation is preferred due to the ease of operation and reduced attrition loss of the valuable catalyst. In this system, a hydrogen-rich gas and the feed mixture are preheated by suitable heating means to the desired reaction temperature and then passed into an isomerization zone containing a fixed bed of catalyst. The isomerization zone may be one or more separate reactors with suitable means therebetween to ensure that the desired isomerization temperature is maintained at the entrance to each reactor. The reactants may be contacted with the catalyst bed in either upward-, downward-, or radial-flow fashion, and the reactants may be in the liquid phase, a mixed liquid-vapor phase, or a vapor phase when contacted with the catalyst.

The alkylaromatic feed mixture, preferably a non-equilibrium mixture of $C_8$ aromatics, is contacted with the isomerization catalyst at suitable alkylaromatic-isomerization conditions. Such conditions comprise a temperature ranging from about 0° to about 600° C. or more, generally within the range of about 100° to about 500° C. or more, and preferably in the range from about 150° to 450° C., or from about 300° to about 500° C. The pressure generally is from about 1 to 100 atmospheres absolute, or may be less than about 50 atmospheres, say, about 10 kPa to about 5 MPa absolute, preferably from about 100 kPa to about 3 MPa absolute. Sufficient catalyst is contained in the isomerization zone to provide a liquid hourly space velocity with respect to the hydrocarbon feed mixture of from about 0.1 to 30 $hr^{-1}$, and preferably 0.5 to 10 $h^{-1}$. The hydrocarbon feed mixture optimally is reacted in admixture with hydrogen at a hydrogen/hydrocarbon mole ratio of about 0.5:1 to about 25:1 or more, say, between about 0.5:1 to 6:1, preferably about 1.5:1 to 5:1. One of the advantages of the processes of this invention is that relatively low partial pressures of hydrogen are still able to provide the sought selectivity and activity of the isomerization and ethylbenzene conversion. Other inert diluents such as nitrogen, argon and light hydrocarbons may be present.

The isomerization conditions may be such that the isomerization is conducted in the liquid, vapor or at least partially vaporous phase. For convenience in hydrogen distribution, the isomerization is preferably conducted in at least partially in the vapor phase. When conducted at least partially in the vaporous phase, the partial pressure of $C_8$ aromatics in the reaction zone is preferably such that at least about 50 mass-% of the $C_8$ aromatics would be expected to be in the vapor phase. Often the isomerization is conducted with essentially all the $C_8$ aromatics being in the vapor phase.

The reaction proceeds via the mechanism of isomerizing xylenes while reacting ethylbenzene to form a xylene mixture via conversion to and reconversion from naphthenes. The yield of xylenes in the product is enhanced by forming xylenes from ethylbenzene. The loss of $C_8$ aromatics through the reaction is low: typically less than about 4 wt-% per pass of $C_8$ aromatics in the feed to the reactor, preferably no more than about 3.5 wt-%, and most preferably less than 3 wt-%.

Usually the isomerization conditions are sufficient that at least about 10%, preferably between about 20 and 50%, of the ethylbenzene in the feed stream is converted. Generally the isomerization conditions do not result in a xylene equilibrium being reached. Often, the mole ratio of xylenes in the product stream is at least about 80%, say between about 85 and 95%, of equilibrium under the conditions of the isomerization. Where the isomerization process is to generate para-xylene, e.g., from meta-xylene, the feed stream contains less than 5 mass-% para-xylene and the isomerization product comprises a para-xylene/xylenes mole ratio of between about 0.20:1 to 0.25:1.

The particular scheme employed to recover an isomerized product from the effluent of the reactors of the isomerization zone is not critical to the instant invention, and any effective recovery scheme known in the art may be used. Typically, the liquid product is fractionated to remove light and/or heavy byproducts to obtain the isomerized product. Heavy byproducts include $A_{10}$ compounds such as dimethylethylbenzene. In some instances, certain product species such as ortho-xylene or dimethylethylbenzene may be recovered from the isomerized product by selective fractionation. The product from isomerization of $C_8$ aromatics usually is processed to selectively recover the para-xylene isomer, optionally by crystallization or by selective adsorption using crystalline aluminosilicates according to U.S. Pat. No. 3,201,491, hereby incorporated herein by reference. Alternative adsorption recovery processes are described in U.S. Pat. Nos. 3,626,020; 3,696,107; 4,039,599; 4,184,943; 4,381,419 and 4,402,832, incorporated herein by reference.

The catalysts used in the processes of this invention comprise a low $Si/Al_2$ MTW type zeolite, also characterized as "low silica ZSM-12", and defined in the instant invention to include molecular sieves with a silica/alumina ratio less than about 45, preferably from about 20 to about 40 or 45, and sometimes 25 to 40. The preparation of the preferred MTW-type zeolites by crystallizing a mixture comprising an alumina source, a silica source and templating agent using methods well known in the art. U.S. Pat. No. 3,832,449, which is herein incorporated by reference, more particularly describes an MTW-type zeolite using tetraalkylammonium cations. U.S. Pat. No. 4,452,769 and 4,537,758, which are incorporated herein by reference, use a methyltriethylammonium cation to prepare a highly siliceous MTW-type zeolite. U.S. Pat. No. 6,652,832 uses a N,N-dimethylhexamethyleneimine cation as a template to produce low silica/alumina ratio MTW type zeolite without MFI impurities. Preferably, high purity crystals are used as seeds for subsequent batches. As stated in the foregoing patents, the original cations of the as-synthesized material can be replaced in accordance with techniques well known in the art, at least in part, by ion exchange with other cations. Preferred replacing cations include hydrogen ions and hydrogen precursor, e.g., ammonium ions and mixtures thereof.

The MTW-type zeolitic components of the catalysts of the present invention is preferably substantially mordenite-free. Substantially mordenite-free is herein defined to mean a MTW component containing less than about 20 wt-% mordenite impurity, preferably less than about 10 wt-%, and most preferably less than about 5 wt-% mordenite which is about at the lower level of detectability using most characterization methods known to those skilled in the art such as X-ray diffraction crystallography. Mordenite can form concurrently with the synthesis of low $Si/Al_2$ MTW. Especially where the silica/alumina ratio of the MTW is lowered, and the concomitant mordenite phase under low silica conditions is minimized, a catalyst composite with excellent properties for low aromatic ring loss when converting ethylbenzene to para-xylene under with minimum benzene by-product production.

The MTW-type zeolite is preferably composited with a binder for convenient formation of catalyst particles. The proportion of zeolite in the catalyst may range from about 1 to about 99 wt-%, and is often about 1 to about 90 wt-%, preferably about 2 to about 60 wt-%, and sometimes, 2 to about 20 wt-%, the remainder other than metal and other components discussed herein being the binder component. Refractory inorganic oxide binders are preferred and the binder should be a porous, adsorptive support having a surface area of about 25 to about 500 $m^2/g$. Suitable binder materials include those which have traditionally been used in hydrocarbon conversion catalysts such as: (1) refractory inorganic oxides such as aluminas, titania, zirconia, chromia, zinc oxide, magnesia, thoria, boria, silica-alumina, silica-magnesia, chromia-alumina, alumina-boria, silica-zirconia, phosphorus-alumina, etc.; (2) ceramics, porcelain, bauxite; (3) silicas or silica gel, silicon carbide, clays and silicates including those synthetically prepared and naturally occurring, which may or may not be acid treated, for example, attapulgite clay, diatomaceous earth, fuller's earth, kaolin, kieselguhr, etc.; (4) crystalline zeolitic aluminosilicates, either naturally occurring or synthetically prepared such as FAU, MEL, MFI, MOR, MTW (IUPAC Commission on Zeolite Nomenclature), in hydrogen form or in a form which has been exchanged with metal cations, (5) spinels such as $MgAl_2O_4$, $FeAl_2O_4$, $ZnAl_2O_4$, $CaAl_2O_4$, and other like compounds having the formula $MOAl_2O_3$ where M is a metal having a valence of 2; and (6) combinations of materials from one or more of these groups.

A preferred refractory inorganic oxide for use in the present invention is alumina. Suitable alumina materials are the crystalline aluminas known as the gamma-, eta-, and theta-alumina, with gamma- or eta-alumina providing the best results.

A suitable shape for the catalyst composite is an extrudate. The well-known extrusion method initially involves mixing of the molecular sieve with optionally the binder and a suitable peptizing agent to form a homogeneous dough or thick paste having the correct moisture content to allow for the formation of extrudates with acceptable integrity to withstand direct calcination. Extrudability is determined from an analysis of the moisture content of the dough, with a moisture content in the range of from about 30 to about 50 wt-% being preferred. The dough is then extruded through a die pierced with multiple holes and the spaghetti-shaped extrudate is cut to form particles in accordance with techniques well known in the art. A multitude of different extrudate shapes is possible, including, but not limited to, cylinders, cloverleaf, dumbbell and symmetrical and asymmetrical polylobates. It is also within the scope of this invention that the extrudates may be further shaped to any desired form, such as spheres, by marumerization or any other means known in the art.

Another suitable shape of the composite is a sphere continuously manufactured by the well-known oil drop method. Preparation of alumina-bound spheres generally involves dropping a mixture of molecular sieve, alumina sol, and gelling agent into an oil bath maintained at elevated temperatures. Alternatively, gelation of a silica hydrosol may be effected using the oil-drop method. One method of gelling this mixture involves combining a gelling agent with the mixture and then dispersing the resultant combined mixture into an oil bath or tower which has been heated to elevated temperatures such that gelation occurs with the formation of spheroidal particles. The gelling agents that may be used in this process are hexamethylene tetraamine, urea or mixtures thereof. The gelling agents release ammonia at the elevated temperatures which sets or converts the hydrosol spheres into hydrogel spheres. The spheres are then continuously withdrawn from the oil bath and typically subjected to specific aging treatments in oil and an ammoniacal solution to further improve their physical characteristics.

Preferably, the resulting composites are then washed and dried at a relatively low temperature of about 50° to 200° C. and subjected to a calcination procedure at a temperature of about 450° to 700° C. for a period of about 1 to about 20 hours.

Catalysts of the invention also comprise a hydrogenation catalyst component, especially a platinum-group metal, including one or more of platinum, palladium, rhodium, ruthenium, osmium, and iridium. The preferred platinum-group metal is platinum. The platinum-group metal component may exist within the final catalyst composite as a compound such as an oxide, sulfide, halide, oxysulfide, etc., or as an elemental metal or in combination with one or more other ingredients of the catalyst composite. It is believed that the best results are obtained when substantially all the platinum-group metal component exists in a reduced state. This component may be present in the final catalyst composite in any amount which is catalytically effective; the platinum-group metal generally will comprise about 0.01 to about 2 wt-% of the final catalyst, calculated on an elemental basis. Excellent results are obtained when the catalyst contains about 0.05 to about 1 wt-% of platinum.

The platinum-group metal component may be incorporated into the catalyst composite in any suitable manner. One method of preparing the catalyst involves the utilization of a water-soluble, decomposable compound of a platinum-group metal to impregnate the calcined sieve/binder composite. Alternatively, a platinum-group metal compound may be added at the time of compositing the sieve component and binder. Complexes of platinum group metals which may be employed in impregnating solutions, co-extruded with the sieve and binder, or added by other known methods include chloroplatinic acid, chloropalladic acid, ammonium chloroplatinate, bromoplatinic acid, platinum trichloride, platinum tetrachloride hydrate, platinum dichlorocarbonyl dichloride, tetramine platinic chloride, dinitrodiaminoplatinum, sodium tetranitroplatinate (II), palladium chloride, palladium nitrate, palladium sulfate, diaminepalladium (II) hydroxide, tetraminepalladium (II) chloride, and the like. It is within the scope of the present invention that the catalyst composites may contain other metal components. Such metal modifiers may include rhenium, tin, germanium, lead, cobalt, nickel, indium, gallium, zinc, uranium, dysprosium, thallium, and mixtures thereof. Catalytically effective amounts of such metal modifiers may be incorporated into the catalysts by any means known in the art to effect a homogeneous or stratified distribution.

A Group IVA (IUPAC 14) metal component is an optional ingredient of the catalyst of the present invention. Of the Group IVA (IUPAC 14) metals, germanium and tin are preferred and tin is especially preferred. This component may be present as an elemental metal, as a chemical compound such as the oxide, sulfide, halide, oxychloride, etc., or as a physical or chemical combination with the porous carrier material and/or other components of the catalyst. Preferably, a substantial portion of the Group IVA (IUPAC 14) metal exists in the finished catalyst in an oxidation state above that of the elemental metal. The Group IVA (IUPAC 14) metal component optimally is utilized in an amount sufficient to result in a final catalyst containing about 0.01 to about 5 wt-% metal, calculated on an elemental basis, with best results obtained at a level of about 0.1 to about 2 wt-% metal.

The optional Group IVA (IUPAC 14) metal component may be incorporated in the catalyst in any suitable manner to achieve a homogeneous dispersion, such as by coprecipitation with the porous carrier material, ion-exchange with the carrier material or impregnation of the carrier material at any stage in the preparation. One method of incorporating the Group IVA (IUPAC 14) metal component into the catalyst composite involves the utilization of a soluble, decomposable compound of a Group IVA (IUPAC 14) metal to impregnate and disperse the metal throughout the porous carrier material. The Group IVA (IUPAC 14) metal component can be impregnated either prior to, simultaneously with, or after the other components are added to the carrier material. Thus, the Group IVA (IUPAC 14) metal component may be added to the carrier material by commingling the latter with an aqueous solution of a suitable metal salt or soluble compound such as stannous bromide, stannous chloride, stannic chloride, stannic chloride pentahydrate; or germanium oxide, germanium tetraethoxide, germanium tetrachloride; or lead nitrate, lead acetate, lead chlorate and the like compounds. The utilization of Group IVA (IUPAC 14) metal chloride compounds, such as stannic chloride, germanium tetrachloride or lead chlorate is particularly preferred since it facilitates the incorporation of both the metal component and at least a minor amount of the preferred halogen component in a single step. When combined with hydrogen chloride during the especially preferred alumina peptization step described hereinabove, a homogeneous dispersion of the Group IVA (IUPAC 14) metal component is obtained in accordance with the present invention. In an alternative embodiment, organic metal compounds such as trimethyltin chloride and dimethyltin dichloride are incorporated into the catalyst during the peptization of the inorganic oxide binder, and most preferably during peptization of alumina with hydrogen chloride or nitric acid.

The catalysts of the present invention may contain a halogen component, comprising either fluorine, chlorine, bromine or iodine or mixtures thereof, with chlorine being preferred. Preferably, however, the catalyst contains no added halogen other than that associated with other catalyst components.

The catalyst composite is dried at a temperature of from about 100° to about 320° C. for a period of from about 2 to about 24 or more hours and, usually, calcined at a temperature of from about 400° to about 650° C. in an air atmosphere for a period of from about 0.1 to about 10 hours until the metallic compounds present are converted substantially to the oxide form. If desired, the optional halogen component may be adjusted by including a halogen or halogen-containing compound in the air atmosphere.

The resultant calcined composites optimally are subjected to a substantially water-free reduction step to ensure a uniform and finely divided dispersion of the optional metallic components. The reduction optionally may be effected in the process equipment of the present invention. Substantially pure and dry hydrogen (i.e., less than 20 vol. ppm $H_2O$) preferably is used as the reducing agent in this step. The reducing agent contacts the catalyst at conditions, including a temperature of from about 200° to about 650° C. and for a period of from about 0.5 to about 10 hours, effective to reduce substantially all of the Group VIII metal component to the metallic state. In some cases the resulting reduced catalyst composite may also be beneficially subjected to presulfiding by a method known in the art such as with neat $H_2S$ at room temperature to incorporate in the catalyst composite from about 0.05 to about 1.0 wt-% sulfur calculated on an elemental basis.

EXAMPLES

The following examples are presented only to illustrate certain specific embodiments of the invention, and should not be construed to limit the scope of the invention as set forth in the claims. There are many possible other variations within the spirit of the invention, as those of ordinary skill in the art will recognize.

Example I

Samples of catalysts comprising zeolites are prepared for comparative pilot-plant testing. First, a Catalyst A is prepared to represent a prior art catalyst for use in a process of isomerization of ethylbenzene to para-xylene with minimal benzene formation Catalyst A contains SM-3 silicoaluminophosphate such as disclosed in U.S. Pat. No. 4,943,424, hereby incorporated by reference, and has characteristics as disclosed in the '424 patent. Following the teachings of U.S. Pat. No. 5,898,090, hereby incorporated by reference, Catalyst A is composited with hydrous alumina and tetramine platinic chloride at a platinum level of 0.4 wt-% on an elemental basis. The composite comprises about 60 wt-% SM-3 and 40 wt-% alumina. The catalyst is calcined and reduced, with the product labeled as Catalyst A.

Example II

Catalysts are prepared containing MTW-type zeolite prepared in accordance with U.S. Pat. No. 4,452,769. To a solution of 0.2 mass-parts sodium hydroxide in 9 mass-parts distilled water are added 0.195 mass-parts aluminum hydroxide hydrate and stirred until dissolved. A second solution of 1.5 mass-parts of methyltriethylammonium chloride in 9 mass-parts distilled water is prepared and stirred until dissolved. Then, both solutions are stirred together until homogenized. Next, 3 mass-parts of precipitated silica are added, stirred for 1 hour at room temperature and sealed in a Teflon-lined autoclave for 8 days at 150° C. Zeolite type MTW is recovered after cooling, filtering, and washing with distilled water. After drying, the recovered product is calcined at 550° C. to remove the template and ion-exchanged three times with $NH_4NO_3$ and dried to show the following analysis: $0.9NH_4$: $Al_2O_3$:$41SiO_2$:$84H_2O$. The X-ray diffraction pattern is consistent with an MTW structure zeolite and no mordenite phase is detected.

To form Catalyst B, about 10 wt % of this MTW-zeolite (dry) is composited with about 90 wt-% alumina to form extruded shaped catalyst particles. The particles are then metal-impregnated using a solution of chloroplatinic acid. Upon completion of the impregnation, the catalyst is dried, oxidized, reduced, and sulfided to yield a catalyst containing about 0.3 wt-% platinum and 0.1 wt-% sulfur. The finished catalyst is labeled Catalyst B.

Example III

Catalysts A and B are evaluated for ethylbenzene isomerization to para-xylene using a pilot plant flow reactor processing a non-equilibrium $C_8$ aromatic feed having the following approximate composition in wt-%:

| | |
|---|---|
| Toluene | 0.2 |
| $C_8$ Non-aromatics | 8.3 |
| Ethylbenzene | 26.8 |
| Para-xylene | 0.9 |
| Meta-xylene | 42.4 |
| Ortho-xylene | 21.0 |
| $C_9^+$ Non-aromatics | 0.4 |

This feed is contacted with catalyst at a pressure of about 620 kPa, a liquid hourly space velocity of 3 $hr^{-1}$, and a hydrogen/hydrocarbon mole ratio of 4. Reactor temperature is adjusted to effect a favorable conversion level. Conversion is expressed as the disappearance per pass of ethylbenzene, and $C_8$ aromatic ring loss is primarily to benzene and toluene, with smaller amounts of light gases being produced. Results are as follows:

| Catalyst | A | B |
|---|---|---|
| Temperature ° C. | 386 | 371 |
| p-xylene/xylenes | 22.5 | 22.3 |
| EB conversion, wt % | 31 | 38 |
| Benzene yield, wt % | 0.25 | 0.10 |
| $C_8$ Ring loss | 2.5 | 2.5 |

Catalyst B shows better conversion of ethylbenzene while minimizing the yield of undesired benzene as compared to Catalyst A. The "$C_8$ ring loss" is in units of mol-% defined as "$(1-(C_8$ naphthenes and aromatics in product)/($C_8$ naphthenes and aromatics in feed))*100", which represents material that is to be circulated to another unit in an aromatics complex. Such circulation is expensive and a low amount of $C_8$ ring loss is a favorable feature of the catalyst of the present invention.

Example IV

Similarly, additional batches of MTW-type zeolite are prepared according to the procedure outlined above in Example II. Due to variations in stirring and seed crystals as well as other inhomogeneous effects among the vessels used, resulting batches have various amounts of impurities at a silica/alumina ratio of about 34. Using X-ray diffraction methods, the impurities are determined to be a mordenite-type zeolite. To understand the effect of the impurity, various samples are obtained and made into catalysts as described below.

Catalyst C is prepared with the same material as Catalyst B, 100 wt-% MTW, see Example II. Catalyst D is prepared with a zeolitic composite comprising 90 wt-% MTW and 10 wt-% mordenite. Catalyst E is prepared with a zeolitic composite comprising 80 wt-% MTW and 20 wt-% mordenite. Finally, Catalyst F is prepared with a zeolitic composite comprising 50 wt-% MTW and 50 wt-% mordenite to illustrate a catalyst with substantial mordenite impurity and thus is not considered a catalyst within the scope of the invention.

Catalysts C through F are formed into extruded particles using about 5 wt-% of the zeolitic composite material above and about 95 wt-% alumina binder. The particles are then metal-impregnated using a solution of chloroplatinic acid. Upon completion of the impregnation, the catalysts are dried, oxidized, reduced, and sulfided to yield catalysts containing about 0.3 wt-% platinum and 0.1 wt-% sulfur. The finished catalysts are labeled respectively, Catalysts C through F.

Example V

Catalysts C through F are evaluated for $C_8$ aromatic ring loss using a pilot plant flow reactor processing a non-equilibrium $C_8$ aromatic feed having the following approximate composition in wt-%:

| $C_8$ Non-aromatics | 7 |
|---|---|
| Ethylbenzene | 16 |
| Para-xylene | <1 |
| Meta-xylene | 52 |
| Ortho-xylene | 25 |

This feed is contacted with a catalyst at a pressure of about 620 kPa, a liquid hourly space velocity of 4 $hr^{-1}$, and a hydrogen/hydrocarbon mole ratio of 4. Reactor temperature is adjusted between about 370° to 375° C. to effect a favorable ethylbenzene conversion level. Results are as follows:

| Catalyst | C | D | E | F |
|---|---|---|---|---|
| p-xylene/xylenes | 22.3 | 22.3 | 22.3 | 22.3 |
| $C_8$ Ring loss | 2.6 | 3.3 | 3.6 | 5.4 |

Catalyst C shows minimum ring loss, and Catalysts D thru F illustrate that mol-% ring loss increases with mordenite impurity level. A low amount of $C_8$ ring loss is a favorable feature of the catalysts of the present invention, which contain MTW-type zeolite substantially free of the mordenite impurity.

Example VI

Catalyst G is prepared to illustrate a bimetallic catalyst of the present invention. Catalyst G is prepared with the same zeolitic material of Catalyst B, 100 wt-% MTW type zeolite (see Example II), and formed into extruded particles using about 5 wt-% of the zeolitic material and about 95 wt-% alumina binder. The particles are then metal-impregnated using a first aqueous solution of tin chloride in a cold rolling evaporative impregnation vessel for about 1 hour and then steamed to dryness. The tin-impregnated base is calcined at 550° C. in air for 2 hours.

Then a second aqueous platinum impregnation is conducted with chloroplatinic acid and similarly cold rolled for 1 hour and steamed to dryness. The catalyst is then oxidized and reduced to produce a finished catalyst containing about 0.3 wt-% of platinum and about 0.1 wt-% of tin, which is labeled as Catalyst G.

Example VII

Catalysts B and G are evaluated for stability in ethylbenzene isomerization to para-xylene using a pilot plant flow reactor processing a non-equilibrium $C_8$ aromatic feed having the same approximate composition as Example III above. This feed is contacted with catalyst at a pressure of about 690 kPa, a weight hourly space velocity of about 9.5 $hr^{-1}$, and a hydrogen/hydrocarbon mole ratio of 4. Reactor temperature is set at 385° C. and conversion is allowed to decline over time.

Results show that Catalyst G has about a 5 wt-% lower initial conversion of ethylbenzene when compared to Catalyst B, but that Catalyst G has a deactivation rate that is only about two-thirds that of Catalyst B. Deactivation rate is determined based on the rate of decline of ethylbenzene conversion over time under the test conditions above.

When a second comparative test is conducted at the same conditions as above except using a 3 $hr^{-1}$ weight hourly space velocity, the ethylbenzene conversion performance of Catalyst G exceeds the performance of Catalyst B after about 130 hours on stream. Thus, Catalyst G shows that superior stability, in terms of decreased deactivation, provides long term value for the isomerization of ethylbenzene into xylenes and that increased yields are produced when conversion is averaged over an extended time period. Moreover, it should be noted that the catalyst performance in terms of $C_8$ ring loss is about equivalent between Catalyst B and Catalyst G.

Example VIII

Samples of catalyst are prepared.

Catalyst H: To a solution of 0.2 mass-parts sodium hydroxide in 9 mass-parts distilled water are added 0.195 mass-parts aluminum hydroxide hydrate and stirred until dissolved. A second solution of 1.5 mass-parts of methyltriethylammonium chloride in 9 mass-parts distilled water is prepared and stirred until dissolved. Then, both solutions are stirred together until homogenized. Next, 3 mass-parts of precipitated silica are added, stirred for 1 hour at room temperature and sealed in a Teflon-lined autoclave for 9 days at 150° C. Zeolite type MTW is recovered after cooling, filtering, and washing with distilled water. After drying, the recovered product is an MTW-type zeolite having the following analysis: $0.24Na_2O:1.0Al_2O_3:34SiO_2:55H_2O:1.2(MTEA-Cl)$. The X-ray diffraction pattern is consistent with an MTW structure zeolite.

The as-synthesized zeolite powder is admixed with a hydrous alumina binder to provide a composite of 5 mass-parts of zeolite to 95 mass-parts of alumina. The composite is extruded to form pellets. The extrudate is calcined in air at 565° C. for 4 hours. The pellets are then ion-exchanged at 88°

C. with a 15 mass-% solution of $NH_4NO_3$, washed, dried and re-calcined in air at 565° C. The pellets are then impregnated with a solution of chloroplatinic acid with 3.5 mass-% hydrochloric acid to provide a final platinum level of 0.31 mass-% on the final catalyst. The impregnated pellets are then oxidized and chloride adjusted at 565° C. to yield 1.22 mass-% chloride on the catalyst, subjected to a reducing environment of hydrogen at 565° C., and sulfided with hydrogen sulfide to yield 0.08 mass-% sulfur on the catalyst.

Catalyst J (Comparative): The starting material is an EUO structure zeolite. See, for instance U.S. Pat. No. 6,057,486 for references for making EUO-type zeolite. The ammonium-form of the zeolite is admixed with a hydrous alumina binder to provide a composite of 10 mass-parts of zeolite to 90 mass-parts of alumina. The composite is extruded to form pellets. The extrudate is calcined in air at 565° C. for 4 hours. The pellets are then impregnated with a solution of chloroplatinic acid with 2.0 mass-% hydrochloric acid to provide a final platinum level of 0.28 mass-% on the final catalyst. The impregnated pellets are then oxidized and chloride adjusted at 565° C. to yield 1.63 mass-% chloride on the catalyst, subjected to a reducing environment of hydrogen at 565° C., and sulfided with hydrogen sulfide to yield 0.09 mass-% sulfur on the catalyst.

Catalyst K (Comparative): An SM-3, crystalline silicoaluminophosphate such as disclosed in U.S. Pat. No. 4,943,424 (Miller) is used to make Catalyst C. The SM-3 is composited with hydrous alumina and tetra-ammine platinum chloride. The composites comprise about 60 mass-% SM-3 and 40 mass-% alumina. Tetra-ammine platinum chloride is incorporated into the composites to effect platinum and chloride contents of 0.39 and 0.21 mass-%, respectively, on an elemental basis, and the catalyst is calcined, reduced and sulfided to yield 0.07 mass-% sulfur.

Catalyst L (Comparative): A spherical catalyst comprising about 10 mass-% MOR in an alumina matrix is prepared by oil dropping according to the teachings of U.S. Pat. No. 2,620,314. The calcined, reduced and sulfided catalyst contains about 0.28 mass-% platinum, 0.86 mass-% chloride and 0.11 mass-% sulfur.

Example IX

Catalysts H, J, K and L are evaluated in a pilot plant for the isomerization of a feed stream containing 16 mass-% ethylbenzene, 25 mass-% ortho-xylene and 52 mass-% meta-xylene. The feed contains 7 mass-% naphthenes. The pilot plant runs are at a hydrogen/hydrocarbon ratio of 4:1. The pilot plant runs are summarized in Table 1. The product data for Catalysts H, J, and K are taken at approximately 200 hours of operation. The data from Catalyst L are taken at 150 hours. The higher activity of Catalyst H requires a higher LHSV for purposes of comparison with Catalysts J, K and L at approximately the same temperatures. The liquid hourly space velocities are based upon the liquid volume of the feed to the pilot plant.

TABLE 1

| Catalyst | H | J Comparative | K Comparative | L Comparative |
|---|---|---|---|---|
| LHSV, $hr^{-1}$ | 3.9 | 2.9 | 3.0 | 3.0 |
| WABT, ° C. | 373 | 380 | 396 | 386 |
| Pressure, kPa g | 570 | 695 | 1020 | 745 |
| Para-xylene/xylene | 22.3 | 22.5 | 22.4 | 22.2 |
| EB Conversion, % | 38 | 20 | 23 | 33 |
| $C_8$ loss, mass % | 3.0 | 4.4 | 4.3 | 5.9 |

TABLE 1-continued

| Catalyst | H | J Comparative | K Comparative | L Comparative |
|---|---|---|---|---|
| $C_7$ and $C_9$ aromatics, mass % of by-products | 52.5 | 34.1 | 41.7 | 50.4 |
| $C_6$ and $C_{10}$ aromatics, mass % of by-products | 8.4 | 5.7 | 12.4 | 16.6 |
| Non-$C_8$ paraffins and naphthenes, mass % of by-products | 39.1 | 60.2 | 45.9 | 33.0 |

The results illustrated in Table 1 demonstrate that Catalyst H, having a low Si/Al MTW-type zeolite, not only exhibits high activity but also low ring loss and importantly, a by-product composition that enhances the recovery of aromatic values. For instance, toluene is the feedstock for a disproportionation unit operation such as disclosed in U.S. Pat. Nos. 4,016,219 and 4,097,543 to make xylenes. Toluene and $C_9$ aromatics can be a feed stock for a transalkylation unit operation such as disclosed in U.S. Pat. No. 4,341,914 to make xylenes.

Example X

Three MTW-containing catalysts are prepared having varying $Si/Al_2$ ratios.

Catalyst M: To a solution of 0.2 mass-parts sodium hydroxide in 9 mass-parts distilled water are added 0.195 mass-parts aluminum hydroxide hydrate and stirred until dissolved. A second solution of 1.5 mass-parts of methyltriethylammonium chloride in 9 mass-parts distilled water is prepared and stirred until dissolved. Then, both solutions are stirred together until homogenized. Next, 3 mass-parts of precipitated silica are added, stirred for 1 hour at room temperature and sealed in a Teflon-lined autoclave for 8 days at 150° C. Zeolite type MTW is recovered after cooling, filtering, and washing with distilled water. After drying, the recovered product is calcined at 550° C. to remove the template and ion-exchanged three times with $NH_4NO_3$ and dried to provide an MTW having the following analysis: $0.9NH_4:Al_2O_3:41 SiO_2:84H_2O$. The X-ray diffraction pattern is consistent with an MTW structure zeolite.

The ammonium form of the zeolite is admixed with a hydrous alumina binder to provide a composite of 10 mass-parts of zeolite to 90 mass-parts of alumina. The composite is extruded to form pellets. The extrudate is calcined in air at 565° C. for 4 hours. The pellets are then impregnated with a solution of chloroplatinic acid with 2.0 mass-% hydrochloric acid to provide a final platinum level of 0.32 mass-% on the final catalyst. The impregnated pellets are then oxidized and chloride adjusted at 565° C. to yield 1.19 mass-% chloride on the catalyst, subjected to a reducing environment of hydrogen at 565° C., and sulfided with hydrogen sulfide to yield 0.07 mass-% sulfur on the catalyst.

Catalyst N (Comparative): To a solution of 0.2 mass-parts sodium hydroxide in 9 mass-parts distilled water are added 0.13 mass-parts aluminum hydroxide hydrate and stirred until dissolved. A second solution of 1.5 mass-parts of methyltriethylammonium chloride in 9 mass-parts distilled water is prepared and stirred until dissolved. Then, both solutions are stirred together until homogenized. Next, 3 mass-parts of precipitated silica are added, stirred for 1 hour at room temperature and sealed in a Teflon-lined autoclave for 8 days at 150° C. Zeolite type MTW is recovered after cooling, filtering, and washing with distilled water. After drying, the recovered product is calcined at 550° C. to remove the template and ion-exchanged three times with NH$_4$NO$_3$ and dried to provide an MTW having the following analysis: 1.4NH$_4$:Al$_2$O$_3$: 62SiO$_2$:10H$_2$O. The X-ray diffraction pattern is consistent with an MTW structure zeolite.

The ammonium form of the zeolite is admixed with a hydrous alumina binder to provide a composite of 10 mass-parts of zeolite to 90 mass-parts of alumina. The composite is extruded to form pellets. The extrudate is calcined in air at 565° C. for 4 hours. The pellets are then impregnated with a solution of chloroplatinic acid with 2.0 mass-% hydrochloric acid to provide a final platinum level of 0.31 mass-% on the final catalyst. The impregnated pellets are then oxidized and chloride adjusted at 565° C. to yield 1.31 mass-% chloride on the catalyst, subjected to a reducing environment of hydrogen at 565° C., and sulfided with hydrogen sulfide to yield 0.09 mass-% sulfur on the catalyst.

Catalyst P (Comparative): To a solution of 0.2 mass-parts sodium hydroxide in 9 mass-parts distilled water are added 0.078 mass-parts aluminum hydroxide hydrate and stirred until dissolved. A second solution of 1.5 mass-parts of methyltriethylammonium chloride in 9 mass-parts distilled water is prepared and stirred until dissolved. Then, both solutions are stirred together until homogenized. Next, 3 mass-parts of precipitated silica are added, stirred for 1 hour at room temperature and sealed in a Teflon-lined autoclave for 8 days at 150° C. Zeolite type MTW is recovered after cooling, filtering, and washing with distilled water. After drying, the recovered product is calcined at 550° C. to remove the template and ion-exchanged three times with NH$_4$NO$_3$ and dried to provide an MTW having the following analysis: 1.5NH$_4$:1Al$_2$O$_3$: 88SiO$_2$:15H$_2$O. The X-ray diffraction pattern is consistent with an MTW structure zeolite.

The ammonium form of the zeolite is admixed with a hydrous alumina binder to provide a composite of 10 mass-parts of zeolite to 90 mass-parts of alumina. The composite is extruded to form pellets. The extrudate is calcined in air at 565° C. for 4 hours. The pellets are then impregnated with a solution of chloroplatinic acid with 2.0 mass-% hydrochloric acid to provide a final platinum level of 0.26 mass-% on the final catalyst. The impregnated pellets are then oxidized and chloride adjusted at 565° C. to yield 1.23 mass-% chloride on the catalyst, subjected to a reducing environment of hydrogen at 565° C., and sulfided with hydrogen sulfide to yield 0.06 mass-% sulfur on the catalyst.

Example XI

Catalysts M, N and P are evaluated in a pilot plant for the isomerization of a feed stream containing 27 mass-% ethylbenzene, 22 mass-% ortho-xylene, 44 mass-% meta-xylene and 7 mass-% naphthenes. The pilot plant runs are at 550 kPa gauge with a hydrogen/hydrocarbon ratio of 4:1. The pilot plant runs are summarized in Table 2. The product data are taken at about 92 hours of operation. The liquid hourly space velocities are based upon the liquid volume of the feed to the pilot plant.

TABLE 2

| Catalyst | M | N Comparative | P Comparative |
|---|---|---|---|
| LHSV, hr$^{-1}$ | 2.9 | 3.0 | 3.0 |
| WABT, ° C. (initial) | 367 | 368 | 368 |
| Pressure, kPa g | 550 | 550 | 550 |
| Para-xylene/xylene | 22.3 | 22.0 | 22.0 |
| EB Conversion, % | 43 | 38 | 31 |
| C$_8$ loss, mass % | 4.1 | 4.3 | 4.9 |
| C$_7$ and C$_9$ aromatics, mass % of by-products | 40.6 | 46.2 | 44.1 |
| C$_6$ and C$_{10}$ aromatics, mass % of by-products | 7.6 | 12.0 | 14.0 |
| Non-C$_8$ paraffins and naphthenes, mass % of by-products | 51.8 | 41.8 | 41.9 |

To maintain a constant para-xylene/xylene ratio at the given LHSV, the temperature of the reactor for Catalyst P needs to be increased from about 368° to 388° C. over 100 to 300 hours on stream. During the same period of time, the reaction temperature for Catalyst E needs to be increased from 368° to 374° C.

The results in Table 2 demonstrate that the low Si/Al ratio MTW type zeolite catalysts used in the processes of this invention reduce ring loss but still have high activities and stabilities.

What is claimed is:

1. A process for converting ethylbenzene to xylenes and isomerizing xylene in a feed stream comprising ethylbenzene and a non-equilibrium mixture of one or more xylenes comprising contacting the feed stream with a catalyst comprising MTW type zeolite having a silica/alumina mole ratio of between about 20:1 and 45:1, from about 0.1 to about 2 wt-% of a platinum-group component calculated on an elemental basis, and from about 0.01 to about 5 wt-% of a tin component calculated on an elemental basis, under isomerization conditions said conditions including the presence of hydrogen in a mole ratio to hydrocarbon of at least about 0.5:1 said feed stream comprising between about 1 and 60 mass-% ethylbenzene and 2 to 20 mass-% naphthenes, to provide a conversion product.

2. The process of claim 1 wherein between about 5 and 35 mass-% of the feed stream is ethylbenzene.

3. The process of claim 1 wherein between about 20 and 50 percent of the ethylbenzene in the feed stream is converted.

4. The process of claim 1 wherein the conversion product contains benzene in an amount of less than about 0.2 wt-% of the feed stream.

5. The process of claim 1 wherein the hydrogen/hydrocarbon ratio is between about 1.5:1 to 6:1.

6. A process for the isomerization of a feed mixture of xylenes and ethylbenzene comprising contacting the feed mixture with a catalyst comprising from about 0.1 to about 2 wt-% of a platinum-group component calculated on an elemental basis, from about 0.01 to about 5 wt-% of a tin component calculated on an elemental basis, from about 1 to about 99 wt-% of a substantially mordenite-free MTW-type zeolite component, having a silica/alumina mole ratio of about 45 or less, and an inorganic-oxide binder component at isomerization conditions comprising a temperature of from about 0° to 600° C., a pressure of from about 1 to 50 atmospheres, a liquid hourly space velocity of from about 0.1 to 30 hr$^{-1}$ and a hydrogen/hydrocarbon mole ratio of from about 0.5:1 to 25:1 to isomerize ethylbenzene to xylenes and obtain an isomerized product comprising a higher proportion of xylenes than in the feed mixture with a C$_8$ aromatics ring loss relative to the feed mixture no more than about 4 mol-%.

7. The process of claim 6 wherein the zeolite silica/alumina ratio is in the range from about 20 to about 40.

8. The process of claim 6 wherein the substantially mordenite-free MTW-type zeolite component comprises less than about 10 wt-% mordenite.

9. The process of claim 6 wherein the substantially mordenite-free MTW-type zeolite component comprises less than about 5 wt-% mordenite.

10. The process of claim 6 further comprising recovery of para-xylene by selective adsorption from the isomerized product.

11. The process of claim 6 further comprising recovery of ortho-xylene from one or both of the isomerized product and the feed mixture.

12. The process of claim 6 wherein the platinum-group metal is platinum.

13. The process of claim 6 wherein the inorganic-oxide binder component is selected from the group consisting of alumina, silica, and mixtures thereof.

14. The process of claim 6 wherein the isomerized product contains benzene in an amount of less than about 0.2 wt-% of the feed mixture.

15. A process for the isomerization of a feed mixture of xylenes and ethylbenzene comprising contacting the feed mixture with a catalyst comprising from about 0.1 to about 2 wt-% of a platinum-group component calculated on an elemental basis, from about 1 to about 99 wt-% of a substantially mordenite-free MTW-type zeolite component, from about 0.01 to about 5 wt-% of a tin component calculated on an elemental basis, having a silica/alumina mole ratio of about 45 or less, and an inorganic-oxide binder component at isomerization conditions comprising a temperature of from about 0° to 600° C., a pressure of from about 1 to 50 atmospheres, a liquid hourly space velocity of from about 0.1 to 30 $hr^{-1}$ and a hydrogen/hydrocarbon mole ratio of from about 0.5:1 to 25:1 to isomerize ethylbenzene to xylenes and obtain an isomerized product comprising a higher proportion of xylenes than in the feed mixture with a $C_8$ aromatics ring loss relative to the feed mixture no more than about 4 mol-%.

* * * * *